United States Patent
Maruyama et al.

(10) Patent No.: US 10,383,902 B2
(45) Date of Patent: Aug. 20, 2019

(54) AGENT FOR PROMOTING GROWTH OF NONPATHOGENIC ORAL INDIGENOUS BACTERIA OR AGENT FOR IMPROVING ORAL BACTERIAL FLORA, AND COMPOSITION FOR ORAL USE

(71) Applicant: HOKUTO CORPORATION, Nagano-shi, Nagano (JP)

(72) Inventors: Masato Maruyama, Tokyo (JP); Toshiaki Kobayashi, Tokyo (JP); Junya Kawai, Nagano (JP); Kenji Ouchi, Nagano (JP); Satoshi Inatomi, Nagano (JP)

(73) Assignee: HOKUTO CORPORATION, Nagano-Shi (JP)

( * ) Notice: Subject to any disclaimer, the term of this patent is extended or adjusted under 35 U.S.C. 154(b) by 0 days.

(21) Appl. No.: 15/511,935

(22) PCT Filed: Sep. 9, 2015

(86) PCT No.: PCT/JP2015/075574
§ 371 (c)(1),
(2) Date: Mar. 16, 2017

(87) PCT Pub. No.: WO2016/043103
PCT Pub. Date: Mar. 24, 2016

(65) Prior Publication Data
US 2017/0252383 A1      Sep. 7, 2017

(30) Foreign Application Priority Data
Sep. 17, 2014   (JP) ................................ 2014-189012

(51) Int. Cl.
*A61K 36/07*      (2006.01)
*A61Q 11/00*      (2006.01)
(Continued)

(52) U.S. Cl.
CPC .............. *A61K 36/07* (2013.01); *A61K 8/022* (2013.01); *A61K 8/9728* (2017.08);
(Continued)

(58) Field of Classification Search
CPC .......... A61K 36/07; A61K 8/96; A61K 36/06; A23L 1/30; A61P 31/04; A61Q 11/00;
(Continued)

(56) References Cited

U.S. PATENT DOCUMENTS 8,183,215 B2   5/2012   Kawakami et al.
2014/0178313 A1   6/2014   Okumura et al.

FOREIGN PATENT DOCUMENTS

JP   63-253019 A   10/1988
JP   8-175946 A   7/1996
(Continued)

OTHER PUBLICATIONS

Yeh et al., (Fish & Shellfish Immunol. vol. 30. Issue 6. Jun. 2011, pp. 1323-1330).*
(Continued)

*Primary Examiner* — Jana A Hines
(74) *Attorney, Agent, or Firm* — Birch, Stewart, Kolasch & Birch, LLP

(57) ABSTRACT

Provided is an agent for promoting growth of nonpathogenic oral indigenous bacteria, or an agent for improving oral bacterial flora, which comprises the dry powder of one or more mushrooms selected from the group consisting of *Hericium erinaceus*, *Grifola frondosa*, *Lyophyllum shimeji*, *Hypsizygus marmoreus*, *Pleurotus ostreatus*, *Agaricus blazei*, and *Lentinula edodes*, or an extract thereof, and which has an excellent growth-promoting effect on non-pathogenic oral indigenous bacteria and an excellent improving effect on oral bacterial flora, and which is effec-
(Continued)

tive in maintaining balanced indigenous bacterial flora. Also provided is a composition for oral use containing same.

2 Claims, 1 Drawing Sheet

(51) Int. Cl.
*A61K 36/06* (2006.01)
*A61K 9/00* (2006.01)
*A61K 9/14* (2006.01)
*A61K 8/9728* (2017.01)
*A61K 8/02* (2006.01)

(52) U.S. Cl.
CPC ............. *A61K 9/0053* (2013.01); *A61K 9/14* (2013.01); *A61K 36/06* (2013.01); *A61Q 11/00* (2013.01)

(58) Field of Classification Search
CPC . C12P 19/18; C12N 1/20; C12R 1/225; C12R 1/46
See application file for complete search history.

(56) References Cited

FOREIGN PATENT DOCUMENTS

| JP | 8-175947 A | 7/1996 | | |
|---|---|---|---|---|
| JP | 2001-151690 A | 6/2001 | | |
| JP | 2003-189817 A | 7/2003 | | |
| JP | 2004-26701 A | 1/2004 | | |
| JP | 2005-320275 A | 11/2005 | | |
| JP | 2007-001961 | * | 1/2007 | ............. A61K 36/07 |
| JP | 2007-1961 A | 1/2007 | | |
| JP | 2010-77028 A | 4/2010 | | |
| JP | 2012-77053 A | 4/2012 | | |
| WO | WO 2012/001347 | * | 1/2012 | ............... A23L 1/28 |
| WO | WO 2013/021957 A1 | 2/2013 | | |

OTHER PUBLICATIONS

Ofek et al., (J. of Biomedicine and Biotech. vol. 2012 Article ID 618314, 2 pages, published 2012). (Year: 2012).*
Hildebrandt et al., Maintaining Mutans Streptococci Suppression with Xylitol Chewing Gum (JADA. vol. 131, Jul. 2000, pp. 909-916). (Year: 2000).*
International Search Report for PCT/JP2015/075574 dated Nov. 17, 2015.
Van Hoogmoed et al., "Inhibition of *Streptococcus* mutans NS Adhesion to Glass with and without a Salivary Conditioning Film by Biosurfactant-Releasing *Streptococcus mitis* Strains", Applied and Environmental Microbiology, Feb. 2000, vol. 66, No. 2, pp. 659-663.
Written Opinion of the International Searching Authority for PCT/JP2015/075574 (PCT/ISA/237) dated Nov. 17, 2015.
Singaporean Search Report and Written Opinion for Singaporean Application No. 11201702011S, dated Feb. 1, 2018.
Aas, J.A., et al, "Defining the Normal Bacterial Flora of the Oral Cavity," Journal of Clinical Microbiology, Nov. 1, 2005, vol. 43, No. 11, pp. 5721-5732.
Ciric, L., et al, "In Vitro Assessment of Shiitake Mushroom (*Lentinula edodes*) Extract for Its Antigingivitis Activity," Journal of Biomedicine and Biotechnology, Jan. 1, 2011, vol. 2011, pp. 1-7.
Daglia, M., et al, "Plant and Fungal Food Components with Potential Activity on the Development of Microbial Oral Diseases," Journal of Biomedicine and Biotechnology, Jan. 1, 2011, vol. 2011, pp. 1-9.
European Search Report for Appl. No. 15842274.1 dated Jun. 19, 2018.

* cited by examiner

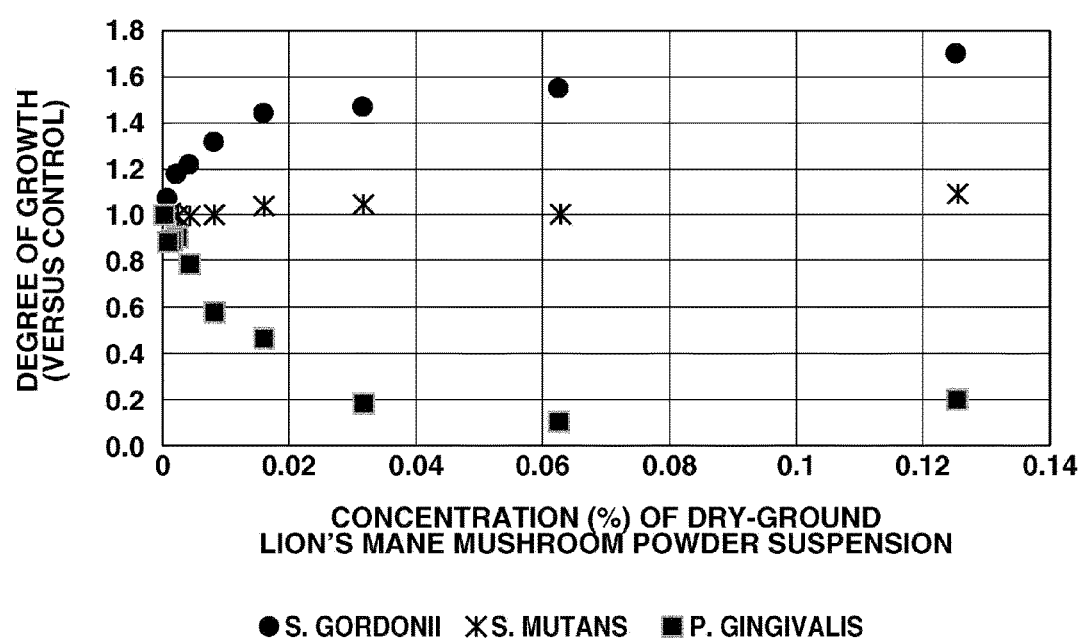

AGENT FOR PROMOTING GROWTH OF NONPATHOGENIC ORAL INDIGENOUS BACTERIA OR AGENT FOR IMPROVING ORAL BACTERIAL FLORA, AND COMPOSITION FOR ORAL USE

TECHNICAL FIELD

The present invention relates to an agent for promoting the growth of non-pathogenic indigenous oral bacteria or an agent for improving the bacterial flora within the oral cavity, which agent has an excellent growth-promoting effect on non-pathogenic indigenous bacteria in the oral cavity and an excellent bacterial flora-improving effect in the oral cavity, and is effective for maintaining a balance of normal oral bacterial flora. The present invention also relates to an oral composition containing the agent thereof.

BACKGROUND ART

A variety of bacteria coexist with the human body, forming bacterial populations which are referred to as normal, or indigenous, bacterial flora. Although pathogens and opportunistic infectious bacteria are present in these normal bacterial flora, when a balance in the bacterial flora is maintained, diseases caused by such bacteria are suppressed, affording a state of health. However, when the balance in the bacterial flora breaks down due to eating habits, the ingestion of antibiotics, stress, aging and the like, the pathogens and opportunistic infectious bacteria increase, leading to illness. Therefore, in order to control illness, it is important not only to suppress pathogens, but also to maintain a balance in the normal bacterial flora by activating non-pathogenic indigenous bacteria.

Of the several hundred species of bacteria that live in the oral cavity, only a few species of bacteria exhibit pathogenicity. These include *Porphyromonas gingivalis*, an organism that causes periodontal disease, and *Streptococcus mutans*, an organism that causes dental caries. Most of the other species are normal bacteria which are generally non-pathogenic in the oral cavity, including the following which typically do not exhibit pathogenicity in humans; bacteria of the genus *Streptococcus* of the *Mitis* group such as *Streptococcus gordonii, Streptococcus mitis* and *Streptococcus oxalis*, bacteria of the genus *Veillonella* such as *Veillonella parvula*, and bacteria of the genus *Neisseria* such as *Neisseria subflaba*. Therefore, to prevent diseases of the oral cavity, it is important to form and maintain within the mouth a good balance of bacterial flora made up of such normal, non-pathogenic bacteria.

In particular, *Mitis* group streptococci are indigenous bacteria which are known to play a role in adherence to the tooth plane of the above dental caries and periodontal disease pathogens and to have antibacterial effects (Non-Patent Document 1), whose use as probiotics has also been disclosed (Patent Document 1: WO 2013/021957), and which act to suppress diseases of the oral cavity.

In this connection, the following art has been disclosed: an agent for improving the bacterial flora in the oral cavity and an agent for promoting the growth of indigenous bacteria, which agents contain ganglioside as an effective ingredient (Patent Document 2: JP-A 2005-320275); art which uses caffeine to improve the oral bacterial flora (Patent Document 3: JP-A 2012-77053); and oral compositions which have an antibacterial activity on dental caries-forming bacteria and also have the effect of increasing lactic acid degrading bacteria (Patent Documents 4 and 5: JP-A H08-175946, JP-A H08-175947). However, the advantageous effects of such art have been inadequate.

PRIOR ART DOCUMENTS

Patent Documents

Patent Document 1: WO 2013/021957
Patent Document 2: JP-A 2005-320275
Patent Document 3: JP-A 2012-77053
Patent Document 4: JP-A H08-175946
Patent Document 5: JP-A H08-175947
Patent Document 6: JP-A 2007-1961
Patent Document 7: JP-A 2010-77028
Patent Document 8: JP-A 2004-26701
Patent Document 9: JP-A 2001-151690

Non-Patent Documents

Non-Patent Document 1: Van Hoogmoed, C G, et al.: Applied Environmental Microbiology, 66(2), p. 659-663 (2000)

SUMMARY OF THE INVENTION

Problems to be Solved by the Invention

Accordingly, there has existed a desire for the development of novel art that can promote the growth of non-pathogenic indigenous bacteria within the oral cavity and improve the bacterial flora in the oral cavity, and which can form and maintain a good balance of normal oral bacterial flora.

It is therefore an object of the present invention to provide an agent for promoting the growth of non-pathogenic indigenous oral bacteria or an agent for improving the bacterial flora in the oral cavity, which agent has an excellent growth-promoting effect on non-pathogenic indigenous bacteria in the oral cavity and an excellent bacterial flora-improving effect in the oral cavity, and is effective for maintaining a balance of normal oral bacterial flora. Another object is to provide an oral composition containing such an agent.

Means for Solving the Problems

The present inventors have conducted extensive investigations in order to attain these objects. As a result, they have found that dried powders of specific mushrooms, or extracts thereof, exhibit excellent effects that promote the growth of non-pathogenic indigenous bacteria and improve the bacterial flora in the oral cavity. They have also found that, by including such a powder or extract in an oral composition, it is possible to impart an excellent growth promoting effect on non-pathogenic indigenous oral bacteria and an excellent bacterial flora improving effect, and to maintain a good balance of normal bacterial flora in the oral cavity.

It is known that mushrooms and mushroom extracts have antibacterial effects on bacteria that cause oral diseases and also have other effects, such as suppressing dental plaque formation and anti-inflammatory effects, and that including these in an oral composition is effective for suppressing dental caries and periodontal disease (Patent Documents 6 to 9: JP-A 2007-1961, JP-A 2010-77028, JP-A 2004-26701, JP-A 2001-151690). However, in the present invention, dried powders of the subsequently described specific mushrooms, or extracts thereof, were unexpectedly found to not exhibit anti bacterial effects against non-pathogenic indigenous bacteria in the oral cavity, but rather to selectively activate their proliferation and promote growth, a hitherto unknown effect. The inventors discovered from this the suitability for use in a new application; namely, as an agent for promoting the growth of non-pathogenic indigenous oral bacteria or an agent for improving the bacterial flora in the oral cavity.

In this invention, the proliferation of non-pathogenic indigenous bacteria within the oral cavity, especially *Mitis* group streptococci selected from among *Streptococcus gordonii, Streptococcus mitis* and *Streptococcus oxalis*, is specifically activated, promoting their growth and enabling the balance of bacterial flora to be improved. As a result, the balance of normal bacterial flora within the oral cavity is prevented from breaking down due to, for example, a disruption in eating habits, thus maintaining a healthy state. Also, *Mitis* group streptococci which play a role in suppressing oral diseases increase, inhibiting oral diseases such as dental caries and periodontal disease, and also making it possible to prevent a tendency toward pathogenicity.

Therefore, this invention is able to provide a preparation which is useful as an agent for promoting the growth of non-pathogenic indigenous bacteria in the oral cavity, and which moreover is particularly useful, via selective promotion of the growth of non-pathogenic indigenous bacteria in the oral cavity, as a bacterial flora improving agent that forms bacterial flora composed primarily of non-pathogenic indigenous bacteria.

Accordingly, the present invention provides the following agent for promoting the growth of non-pathogenic indigenous oral bacteria or agent for improving bacterial flora, and the following oral composition containing such an agent.

[1] An agent for promoting the growth of non-pathogenic indigenous oral bacteria or an agent for improving bacterial flora in the oral cavity, comprising a dry powder of one or more mushroom selected from the group consisting of lion's mane mushroom (*Hericium erinaceus*), maitake (*Grifola frondosa*), hon-shimeji (*Lyophyllum shimeji*), buna-shimeji (*Hypsizygus marmoreus*), oyster mushroom (*Pleurotus ostreatus*), agaricus (*Agaricus blazei*) and shiitake (*Lentinula edodes*), or an extract thereof.

[2] The growth promoting agent or bacterial flora improving agent of [1], wherein the dry mushroom powder or extract thereof is a dry-ground powder of the mushroom fruiting body, or a water extract thereof.

[3] The growth promoting agent or bacterial flora improving agent of [1] or [2], wherein the mushroom is lion's mane mushroom (*Hericium erinaceus*).

[4] The growth promoting agent or bacterial flora improving agent of [1], [2] or [3], wherein the non-pathogenic indigenous oral bacteria are *Mitis* group streptococci selected from the group consisting of *Streptococcus gordonii, Streptococcus mitis* and *Streptococcus oxalis*.

[5] The growth promoting agent or bacterial flora improving agent of any one of [1] to [4], wherein a concentration of the dry mushroom powder or extract thereof is from 0.001 to 50 wt % as dry mushroom powder basis.

[6] An oral composition comprising the growth promoting agent or bacterial flora improving agent of any one of [1] to [5].

[7] The oral composition of [6], wherein a content of the dry mushroom powder or extract thereof included in the growth promoting agent or bacterial flora improving agent is from 0.001 to 50 wt % as dry mushroom powder basis of the overall composition.

[8] The oral composition of [6] or [7] which is prepared in a dosage form selected from the group consisting of tablets, granules, gumdrops, beverages, dentifrices, mouthwashes and mouth sprays.

Advantageous Effects of the Invention

This invention makes it possible to provide an agent for promoting the growth of non-pathogenic indigenous oral bacteria or an agent for improving the bacterial flora in the oral cavity, which agent has an excellent growth-promoting effect on non-pathogenic indigenous bacteria within the oral cavity and an excellent bacterial flora improving effect, and is effective for maintaining a balance of normal oral bacterial flora. The invention also makes it possible to provide an oral composition containing such an agent.

BRIEF DESCRIPTION OF THE DIAGRAM

FIG. 1 is a graph showing the degree of growth of oral bacteria at various concentrations of the dry-ground lion's mane mushroom powder suspension in Experimental Example 1.

EMBODIMENT FOR CARRYING OUT THE INVENTION

The invention is described more fully below. The inventive agent for promoting the growth of non-pathogenic indigenous oral bacterial or agent for improving bacterial flora contains as the effective ingredient a dry mushroom powder or an extract thereof. This selectively activates the proliferation of non-pathogenic indigenous bacteria within the oral cavity, promoting growth of these bacteria and improving the bacterial flora.

Here, the non-pathogenic indigenous oral bacteria are bacteria which grow in the oral cavity and normally do not exhibit pathogenicity in humans. Specific examples include bacteria of the genus *Streptococcus* (i.e., streptococci) such as *Streptococcus gordonii, Streptococcus mitis* and *Streptococcus oralis*; bacteria of the genus *Veillonella* such as *Veillonella parvula*; and bacteria of the genus *Neisseria* such as *Neisseria subflaba*. In this invention, the proliferating and activating effects on *Mitis* group streptococci selected from among *Streptococcus gordonii, Streptococcus mitis* and *Streptococcus oralis* are particularly outstanding.

One or more type of mushroom selected from among lion's mane mushroom (*Hericium erinaceus*), maitake (*Grifola frondosa*), hon-shimeji (*Lyophyllum shimeji*), buna-shimeji (*Hypsizygus marmoreus*), oyster mushroom (*Pleurotus ostreatus*), agaricus (*Agaricus blazei*) and shiitake (*Lentinula edodes*) is used in this invention. A single type of mushroom may be used alone. Alternatively, two or more types of mushroom may be used in combination to achieve an advantageous effect. Of these mushrooms, using lion's mane mushroom, maitake, hon-shimeji and *agaricus*, and especially lion's mane mushroom, is preferred because the proliferation activating effect on non-pathogenic indigenous bacteria in the oral cavity is high, enabling excellent growth-promoting and bacterial flora-improving effects to be conferred.

The dry mushroom powder or extract thereof may be prepared by a known method by using the above mushrooms as the starting material.

In this case, the starting material may be either the mushroom fruiting body or mycelium alone, or both may be used, although using the fruiting body of the mushroom is preferred. The fruiting body is customarily eaten and thus preferable in terms of safety.

The dry mushroom powder may be obtained by employing an ordinary method without particular limitation as the method of preparation. A dry-ground powder obtained by freeze-drying or heat drying, and subsequently grinding, the mushroom fruiting body or mycelium serving as the starting material may be used. The freeze drying or heat drying conditions may be the same as in customary methods. The particle size and other properties of the dry powder are not particularly limited, so long as it is possible to use the dry powder by dispersion, suspension or the like in water.

The mushroom extract can be directly extracted from the mushroom fruiting body and/or mycelium serving as the starting material, although it is preferably obtained by solvent extraction of the dry mushroom powder.

The method of obtaining the extract is not particularly limited. A known method may be employed.

Examples of the extracting solvent include polar solvents and non-polar solvents, such as water, alcohols (e.g., lower alcohols having 1 to 3 carbon atoms, such as methanol, anhydrous ethanol and ethanol; and polyhydric alcohols such as propylene glycol and 1,3-butylene glycol), ketones such as acetone; diethyl ether, dioxane, acetonitrile, esters such as ethyl acetate; xylene, benzene, and chloroform. These may be used singly, or two or more may be combined in any way and used as a mixed solution. It is also possible to combine extracts obtained by extraction with different solvents, and to use them together as a solvent extract. Of the above solvents, particularly when taking into account their use in the human body, water and/or ethanol are preferred from the standpoint of safety. In this invention, when extraction is carried out using in particular a polar solvent, especially water which has a high polarity, the propagation activating effect on non-pathogenic indigenous oral bacteria increases, resulting in even better growth promoting and bacterial flora-improving effect.

The amount of solvent used in the starting material, the extraction temperature and the extraction time may be suitably adjusted without particular limitation.

The resulting extract can be prepared by optionally carrying out drying, concentration or dilution, etc. according to the dosage form and physical form of the preparation to be used. In many cases, the extract may be used directly in the state in which it is obtained. However, within a range that does not detract from the potency of the extract, where necessary, it is also possible to add purifying treatment such as deodorization or decolorization or to carry out filtration with a sterile filter, and to optionally select and carry out ordinary means commonly employed for extracts.

In this invention, of the above, it is preferable to use as the dry mushroom powder or extract thereof, a dry-ground powder of the mushroom fruiting body or a water extract thereof, with the use of a dry-ground powder of the mushroom fruiting body being especially preferred. The dry-ground powder may be used directly as is, although use as a suspension obtained by dispersion in water is preferred. Using these, the growth promoting effect on non-pathogenic indigenous bacteria within the oral cavity and the bacterial flora improving effect are even better. In addition, when the dry-ground powder is used as, preferably, an aqueous suspension, satisfactory effects can be achieved at lower concentrations than when an extract is used.

The above dry powder is preferably one in which at least 95 wt % of the particles have a size of 500 μm or less, and more preferably one in which at least 95 wt % of the particles have a size of 150 μm or less. A dry powder in which the particle size is 500 μm or less is made of particles that pass through a 30 mesh size (JIS standards) sieve. A dry powder in which the particle size is 150 μm or less can be obtained using a 100 mesh (JIS standards) sieve.

The dry mushroom powder or extract thereof preferably has a concentration (dry mushroom powder basis) of from 0.001 to 50% (here and below, "%" stands for percent by weight), more preferably from 0.01 to 20%, and even more preferably from 0.1 to 20%. Within this concentration range, proliferation of the non-pathogenic indigenous bacteria is activated, enabling growth to be further promoted and enabling the bacterial flora to be better improved. However, when the concentration is too high, antibacterial effects against non-pathogenic indigenous bacteria may arise as well. This can be adequately prevented by setting the concentration to 50% or less. When using an extract, the "dry mushroom powder basis" amount refers to the concentration calculated from the amount of dry mushroom powder required to obtain the amount of mushroom extract to be used (the same applies below).

The dry mushroom powder or extract thereof according to the invention can be suitably included within oral compositions as an agent for promoting the growth of non-pathogenic indigenous oral bacterial or for improving the bacterial flora in the oral cavity. Specifically, it can be rendered into such physical forms as a solid, liquid, paste or gel, and can be prepared into various dosage forms, including chewing gum, tablets such as troche, tablet and candy; granules, gumdrops, beverages such as powder beverage; dentifrices such as toothpaste, liquid-like dentifrice, liquid dentifrice and moistened powder dentifrice; mouthwashes, and mouth sprays. Chewing gum, tablets such as troche, tablet and candy; granules, gumdrops and beverages are especially preferred.

The content of the dry mushroom powder or extract thereof in the overall composition is preferably within the above concentration range. The content on a dry powder basis is preferably from 0.001 to 50%, more preferably from 0.01 to 20%, and even more preferably from 0.1 to 20%. Within this concentration range, the proliferation of non-pathogenic indigenous bacteria is further activated, enabling growth to be further promoted and the bacterial flora to be further improved.

At a higher concentration, particularly one that exceeds 0.1%, the non-pathogenic indigenous bacterial growth promoting effect may increase and antibacterial effects against pathogenic bacteria such as *Porphyromonas gingivalis* may be also fully exhibited. At 50% or less, the antibacterial effects against non-pathogenic indigenous bacteria may be suppressed, which is desirable for fully promoting the growth of non-pathogenic indigenous bacteria.

In addition to the above ingredients, known ingredients suitable for the dosage form may be optionally included in oral compositions, insofar as doing so does not detract from the advantageous effects of the invention, and preparation may be carried out by an ordinary method.

For example, the following may be included in chewing gum: a gum base, binders such as an edible gum; sweeteners, colorants, acidulants, preservatives, brighteners, flavors, and effective ingredients. In addition, the chewing gum may be optionally coated with a sugar coating.

The following may be included in tablets: sugar alcohols such as sorbitol and maltitol; excipients such as cellulose, lactose and dextrin; finely divided silicon dioxide, acidulants, sweeteners, colorants, emulsifiers, thickeners, gelatinizing agents, fruit juices, spices, and effective ingredients.

The following may be included in gumdrops: thickeners and gelatinizing agents such as glycerol and gelatin; sugars, acidulants, sweeteners, colorants, emulsifiers, fruit juices, and effective ingredients.

The following may be included in dentifrices: abrasives, humectants, binders, surfactants, sweeteners, colorants, preservatives, flavors, and effective ingredients.

Specific examples of gum bases that may be used in chewing gum include commercial gum bases containing gum base resins such as polyvinyl acetate resin, natural resins and ester gums; emulsifying agents, fillers such as calcium carbonate, calcium phosphate and talc; and plasticizers and softeners, such as lanolin, stearic acid and salts thereof; and glycerol.

Examples of sweeteners include sugars such as sucrose, glucose, dextrose, invert sugar and fructose; sugar alcohols such as maltitol, xylitol, erythritol and sorbitol; and saccharin and aspartame.

Examples of abrasives that may be used in dentifrices include abrasives such as silica abrasives, calcium phosphate abrasives, and calcium carbonate. The content thereof is generally from 2 to 50% in toothpastes, and from 0 to 30% in liquid-like dentifrices.

Examples of humectants include sugar alcohols such as sorbitol and xylitol; and polyhydric alcohols such as glycerol and propylene glycol. The content thereof is generally from 5 to 50%.

Examples of binders include organic or inorganic binders such as cellulose derivatives such as sodium carboxymethylcellulose; gums such as xanthan gum; and gelling silica and gelling aluminum silica. The content thereof is generally from 0.5 to 10%.

Surfactants that may be included are exemplified by anionic surfactants, nonionic surfactants, cationic surfactants and amphoteric surfactants that are generally used in oral compositions. Examples of anionic surfactants include alkyl sulfates such as sodium lauryl sulfate, and N-acyl sarcosinates. Examples of nonionic surfactants include sugar fatty acid esters such as sucrose fatty acid esters; sugar alcohol fatty acid esters, sorbitan fatty acid esters, glycerol fatty acid esters, polyoxyethylene fatty acid esters such as polyoxyethylene hydrogenated castor oils; polyoxyethylene higher alcohol ethers, and fatty acid alkanolamides. Examples of cationic surfactants include alkyl ammonium salts. Examples of amphoteric surfactants include betaine-type surfactants and imidazoline-type surfactants. The surfactant content is generally from 0 to 10%, and especially from 0.01 to 5%.

Examples of colorants include Red No. 2, Blue No. 1, and Yellow No. 4. Exemplary preservatives include p-hydroxybenzoate esters.

Known flavor ingredients that are used in oral compositions may be used as the flavor. Illustrative examples include natural flavors such as peppermint oil, spearmint oil, anise oil, eucalyptus oil, wintergreen oil, cinnamon oil, clove oil, thyme oil, sage oil, lemon oil, orange oil, mentha oil, cardamom oil, coriander oil, mandarin oil, lime oil, lavender oil, rosemary oil, laurel oil, chamomile oil, caraway oil, marjoram oil, bay oil, lemongrass oil, origanum oil, pine needle oil, neroli oil, rose oil, jasmine oil, grapefruit oil, sweetie oil, yuzu oil, iris concrete, absolute peppermint, absolute rose and orange flower; flavors obtained by the processing and treatment (head cut, tail cut, fractional distillation, liquid-liquid extraction, essence preparation, powdered flavor preparation) of these natural flavors; single flavors such as menthol, carvone, anethole, cineol, methyl salicylate, cinnamic aldehyde, eugenol, 3-l-methoxypropane-1,2-diol, thymol, linalool, linalool acetate, limonene, menthone, menthyl acetate, N-substituted-p-menthane-3-carboxamide, pinene, octyl aldehyde, citral, pulegone, carvyl acetate, anise aldehyde, ethyl acetate, ethyl butyrate, allyl cyclohexane propionate, methyl anthranilate, ethyl methylphenylglycidate, vanillin, undecalactone, hexanal, butanol, isoamyl alcohol, hexenol, dimethyl sulfide, cyclotene, furfural, trimethylpyrazine, ethyl lactate and ethyl thioacetate; and blended flavors such as strawberry flavor, apple flavor, banana flavor, pineapple flavor, grape flavor, mango flavor, butter flavor, milk flavor, fruit mix flavor and tropical fruit flavor.

The content of these flavors is generally from 0.001 to 50% in chewing gums, tablets, granules, gumdrops and beverages; and from 0.00001 to 1% in dentifrices, mouthwashes and mouth sprays. Perfume flavors using the above flavorants are preferably included in an amount of from 0.1 to 10% within the composition.

Known effective ingredients that are normally included in oral compositions may be included within a range that does not detract from the advantageous effects of the invention. Illustrative examples of effective ingredients include nonionic bactericides such as isopropyl methylphenol; cationic bactericides such as cetylpyridium chloride; anti-inflammatory agents such as tranexamic acid and ε-aminocaproic acid; enzymes such as dextranase; fluorides such as sodium fluoride and sodium monofluorophosphate; water-soluble phosphoric acid compounds, copper compounds, potassium nitrate, aluminum lactate, various types of vitamins, and plant extracts. The content of these effective ingredients is an effective amount within a range that does not detract from the advantageous effects of the invention.

EXAMPLES

The invention is illustrated more fully below by way of Experimental Examples and Formulation Examples, although the invention is not limited by these Examples. In the Examples that follow, unless noted otherwise, all references to percent (%) are by weight.

Experimental Example 1

(1) Method of Preparing Dry Powder of Lion's Mane Mushroom

The fruiting body of lion's mane mushroom (*Hericium erinaceus*) was dried under heating at 60 to 70° C., and the dried fruiting body was ground using a mill, thereby preparing a dry-ground powder. The dry-ground powder was applied to a 100 mesh sieve, and the ground powder that passed through the sieve was used in the test.

(2) Method of Evaluating Effects on Growth of Oral Bacteria

The dry-ground powder of lion's mane mushroom obtained by the above method was dispersed in distilled water, and 100 μL portions of the dispersion were added to a 96-well plate. This dispersion of dry-ground lion's mane mushroom powder was serially 2-fold diluted with 100 μL of distilled water and thus diluted stepwise to one-half the concentration, thereby preparing a two-fold concentration series as shown in FIG. 1. Next, 100 μL of the various bacterial suspensions indicated below were added to the suspensions of dry-ground lion's mane mushroom powder at various concentrations, and cultured anaerobically at 37° C. for about 20 hours. The bacterial suspensions used were prepared by pre-culturing bacteria in a tryptic soy medium (TS medium; Becton and Dickinson) to which 0.0005% hemin and 0.0001% menadione had been added, and inoculating the pre-cultured bacteria to a 2% concentration in a 2-fold concentration TS medium.

Bacterial proliferation was measured as the turbidity at a wavelength of 550 nm, and evaluated by calculating, as the degree of bacterial growth, the relative value with respect to the turbidity of a control that contains no sample (0%). At a degree of growth larger than 1, growth is promoted, with the growth-promoting effect being larger at higher numerical values. Values lower than 1 signify that growth is suppressed. The results are shown in FIG. 1.

The indigenous oral bacteria used for evaluation were of the following three species purchased from the American Type Culture Collection (ATCC).

Non-pathogenic bacterium:
Streptococcus gordonii ATCC 10558 (abbreviated below as S. gordonii)
Pathogenic bacteria:
Streptococcus mutans ATCC 25175 (abbreviated below as S. mutans)
Porphyromonas gingivalis ATCC 33277 (abbreviated below as P. gingivalis)

Prior to turbidity measurement, the culture fluid was stirred by shaking the plate.

From the results in FIG. 1, it is apparent that dry-ground lion's mane mushroom powder exhibits antibacterial properties against the pathogenic bacterium P. gingivalis, but has a growth-promoting action on the non-pathogenic indigenous bacterium S. gordonii. Substantially no antibacterial action or growth-promoting action with respect to the pathogenic bacterium S. mutans was observed.

Experimental Example 2

(1) Method of Preparing Dry-Ground Mushroom Powders and Extracts

The fruiting bodies of lion's mane mushroom, maitake (Grifola frondosa), hon-shimeji (Lyophyllum shimeji), buna-shimeji (Hypsizygus marmoreus), oyster mushroom (Pleurotus ostreatus), agaricus (Agaricus blazei) and shiitake (Lentinula edodes) were freeze-dried by being held at −20° C. for one day. The freeze-dried fruiting bodies were then ground up with a mill, thereby preparing a dry-milled powder. The dry-milled powder was applied to a 100 mesh sieve, and the milled powder that passed through the sieve was used in the test.

In addition, a mushroom extract was prepared as follows. First, 2 mL of distilled water was added to about 0.1 g of the dry-ground mushroom powder obtained by the above method so as to form a 5% suspension, and extraction was carried out by heating the suspension at 80° C. for about 4 hours. The extract was subsequently centrifuged at 10,000 G for 10 minutes, and the resulting supernatant was filtered using a sterile filter having a pore size of 0.22 μm.

(2) Method of Evaluating Growth-Promoting Effects on Normal Bacteria in Oral Cavity Dry-ground mushroom powder suspensions obtained by dispersing the dry-ground powders of various mushrooms prepared as described above to a concentration of 0.01% in distilled water, and 4% aqueous solutions of the various mushroom extracts obtained as described above, were each added as samples in 100 μL portions to 96-well plates. Because the dry-ground mushroom suspensions used to carry out extractions had a concentration of 5%, a 4% aqueous solution of mushroom extract corresponds to a dry powder basis concentration of 0.2% (4×5÷100%).

Next, 100 μL of suspensions of the bacteria shown in Tables 1 and 2 were added to the dry-ground mushroom powder suspensions and mushroom extracts serving as these samples, and the bacteria were cultured aerobically at 37° C. for 12 hours. The bacterial suspensions used were prepared by pre-culturing the bacteria in a tryptic soy medium (TS medium; Becton and Dickinson), and inoculating the pre-cultured bacteria to a 2% concentration in a 2-fold concentration TS medium.

Bacterial proliferation was measured, calculated and evaluated in the same way as in Experimental Example 1. The results are presented in Tables 1 and 2.

The indigenous oral bacteria used in evaluation were of the following three species purchased from the ATCC.

Non-pathogenic bacteria:
Streptococcus gordonii ATCC 10558 (S. gordonii)
Streptococcus mitis ATCC 47456 (abbreviated below as S. mitis)
Streptococcus oralis ATCC 9811 (abbreviated below as S. oralis)

Prior to turbidity measurement, the culture fluids were stirred by shaking the plates.

TABLE 1

Degree of bacterial growth due to dry-ground powders of various mushrooms

| Bacterial species | Lion's mane mushroom | Maitake | Hon-shimeji | Buna-shimeji | Oyster mushroom | Agaricus | Shiitake | Triclosan |
|---|---|---|---|---|---|---|---|---|
| S. gordonii | 2.1 | 1.8 | 1.9 | 1.3 | 1.2 | 2 | 1.5 | 0 |
| S. mitis | 1.5 | 1.5 | 1.5 | 1.2 | 1.3 | 1.8 | 1.3 | 0 |
| S. oralis | 1.9 | 1.8 | 1.8 | 1.2 | 1.3 | 1.8 | 1.2 | 0 |
| | Working Example | | | | | | | Reference Example |

TABLE 2

Degree of bacterial growth owing to extracts of various mushrooms

| Bacterial species | Lion's mane mushroom | Maitake | Hon-shimeji | Buna-shimeji | Oyster mushroom | Agaricus | Shiitake |
|---|---|---|---|---|---|---|---|
| S. gordonii | 1.8 | 1.6 | 1.6 | 1.5 | 2.0 | 1.7 | 1.7 |
| S. mitis | 1.6 | 1.5 | 1.3 | 1.6 | 2.2 | 1.5 | 1.5 |
| S. oralis | 1.4 | 1.3 | 1.1 | 1.4 | 1.7 | 1.4 | 1.4 |
| | Working Example | | | | | | |

As shown in Tables 1 and 2, the antibacterial agent triclosan suppressed growth of the non-pathogenic indigenous bacteria *S. gordonii*, *S. mitis* and *S. oxalis*, but the dry-ground powders and water extracts of mushrooms promoted the growth of these non-pathogenic indigenous bacteria.

Moreover, it was found that when the dry-ground mushroom powders were used in a water-suspended state, advantageous effects emerged at a lower concentration than when water extracts were used.

These results demonstrate that dry powders of mushrooms selected from among lion's mane mushroom, maitake, honshimeji, buna-shimeji, oyster mushroom, *agaricus* and shiitake, and extracts of these powders, are useful as agents for promoting the growth of non-pathogenic indigenous bacteria in the oral cavity and moreover, by selectively promoting the growth of non-pathogenic indigenous bacteria, are useful particularly as bacterial flora-improving agents that form bacterial flora composed primarily of non-pathogenic indigenous bacteria.

Experimental Example 3

(1) Method of Preparing Dry Powder of Lion's Mane Mushroom

The fruiting body of lion's mane mushroom was dried under heating at 60 to 70° C., and the dried fruiting body was ground using a mill, thereby preparing a dry-ground powder. The dry-ground powder was applied to a 100 mesh sieve, and the ground powder that passed through the sieve was used in the test.

(2) Method of Evaluating Growth Promoting Effects (Concentration Dependence) on Indigenous Oral Bacteria The dry-ground powder of lion's mane mushroom thus obtained was dispersed in distilled water, and 100 μL portions of the dispersion were added to a 96-well plate. This dispersion of dry-ground lion's mane mushroom powder was serially 2-fold diluted with 100 μL of distilled water and thus diluted stepwise to one-half the concentration, thereby preparing the concentration series shown in Table 3. The degree of growth by non-pathogenic bacteria (*S. gordonii*) was measured in the same way as in Experimental Example 1 for the dry-ground lion's mane mushroom powder suspensions at various concentrations. The concentrations are dry powder basis values. The results are presented in Table 3.

TABLE 3

Degree of bacterial growth due to aqueous suspensions of dry-ground powder of lion's mane mushroom (concentration dependence)

| Bacterial species | Concentration of dry-ground lion's mane mushroom powder suspension |||||||| 
|---|---|---|---|---|---|---|---|---|
| | 0 | 0.001% | 0.002% | 0.004% | 0.008% | 0.016% | 0.031% | 0.063% |
| *S. gordonii* | 1.00 | 1.37 | 1.52 | 2.00 | 2.05 | 2.47 | 2.46 | 2.51 |
| | Control | | | Working Example |||||

Table 3 demonstrates that at the concentrations investigated, starting from 0.001%, the growth of non-pathogenic bacteria is promoted in a concentration-dependent manner and these effects reach a substantially saturated state at about 0.03%.

Experimental Example 4

(1) Method of Preparing Dry Powder of Lion's Mane Mushroom

The fruiting body of lion's mane mushroom was dried under heating at 60 to 70° C., and the dried fruiting body was ground using a mill, thereby preparing a dry-ground powder. The dry-ground powder was applied to a 100 mesh sieve, and the ground powder that passed through the sieve was used in the test.

(2) Method for Evaluating Bacterial Flora-Improving Effects in Oral Cavity

In order to evaluate the bacterial flora-improving effects in the oral cavity, a crossover test on eight subjects was carried out using the dry lion's mane mushroom powder obtained as described above. Bacteria within each subject's mouth were removed by carrying out oral cleaning, after which the subject ingested 100 mL of a hot water suspension (95° C.) of dry lion's mane mushroom powder at the concentrations shown in Table 4 below over a period of about 10 minutes. The bacterial flora within the mouth 5 hours after ingestion were evaluated. Evaluation of the bacterial flora was carried out by measuring, within mouthrinsed water, the viable counts of streptococci (including the *Mitis* group) as indigenous bacteria and of black pigment-producing bacteria that cause periodontal disease and halitosis as pathogenic bacteria, and determining the constituent ratio of the respective bacteria based on the overall count of indigenous bacteria and pathogenic bacteria. The mouthrinsed water was the expectorated saliva recovered after holding 10 mL of distilled water in the mouth and mouthwashing for about 30 seconds. A *mitis salivarius* plate medium (Becton and Dickinson) was used to measure the indigenous bacteria, and a blood plate medium* to which 200 μg/mL kanamycin had been added was used to measure the pathogenic bacteria. Culturing of the bacteria was carried out for about one week at 37° C. and under anaerobic conditions (80 vol % nitrogen, 10 vol % carbon dioxide, 10 vol % hydrogen), and calculation involved counting the number of colonies that grew.

*Blood plate medium composition (amounts shown as weight per liter)

| | |
|---|---|
| Todd Hewitt broth (Becton and Dickinson) | 30 g/L |
| Agar (Becton and Dickinson) | 15 g/L |
| Hemin (Sigma Aldrich) | 5 mg/L |
| Vitamin K (Wako Pure Chemical Industries, Ltd.) | 1 mg/L |

-continued

*Blood plate medium composition (amounts shown as weight per liter)

| | |
|---|---|
| Distilled water (The total volume was brought up to one liter, followed by 20 minutes of autoclaving at 121° C.) | balance |
| Defibrinated sheep blood (Nippon Bio-Test Laboratories, Inc.) | 100 mL |

TABLE 4

| Dry lion's mane mushroom powder concentration (%) | Constituent ratio of different bacteria (%) | |
|---|---|---|
| | Pathogenic bacteria | Indigenous bacteria |
| 0 | 22.6 | 77.4 |
| 0.15 | 17.8 | 82.2 |
| 0.4 | 15.3 | 84.7 |
| 0.8 | 15.3 | 84.2 |

Table 4 shows that, with the ingestion of a dry lion's mane mushroom powder suspension, a bacterial flora composed primarily of indigenous bacteria formed wherein, relative to no ingestion (0%), the ratio of indigenous bacteria 5 hours after ingestion rose and the ratio of pathogenic bacteria fell.

Next, Formulation Examples are given. The oral compositions containing dry mushroom powders and extracts thereof in the respective Examples had excellent growth promoting effects on non-pathogenic indigenous bacteria in the oral cavity and excellent bacterial flora-improving effects.

In each Example, the dry-ground mushroom powder was applied to a 100 mesh sieve, and the ground powder that passed through the sieve was used in the tests.

[Formulation Example 1] Chewing Gum

| | |
|---|---|
| Xylitol | 49 |
| Maltitol | 20 |
| Gum base | 20 |
| Dry powder of lion's mane mushroom | 1 |
| Gum arabic | 9 |
| Flavor | 1 |
| Total | 100% |

[Formulation Example 2] Chewing Gum

| | |
|---|---|
| Xylitol | 45 |
| Maltitol | 20 |
| Gum base | 20 |
| Dry powder of hon-shimeji | 5 |
| Gum arabic | 9 |
| Flavor | 1 |
| Total | 100% |

[Formulation Example 3] Tablets

| | |
|---|---|
| Sorbitol | 70 |
| Maltitol | 5 |
| Dry powder of lion's mane mushroom | 20 |
| Flavor | 4.5 |
| Finely divided silicon dioxide | 0.5 |
| Total | 100.0% |

[Formulation Example 4] Tablets

| | |
|---|---|
| Sorbitol | 70 |
| Maltitol | 5 |
| Dextrin | 10 |
| Dry shiitake powder | 10 |
| Flavor | 4.5 |
| Finely divided silicon dioxide | 0.5 |
| Total | 100.0% |

[Formulation Example 5] Tablets

| | |
|---|---|
| Sorbitol | 75 |
| Maltitol | 5 |
| Dextrin | 10 |
| Dry powder of oyster mushroom | 5 |
| Flavor | 4.5 |
| Finely divided silicon dioxide | 0.5 |
| Total | 100.0% |

[Formulation Example 6] Tablets

| | |
|---|---|
| Sorbitol | 79 |
| Maltitol | 5 |
| Dextrin | 10 |
| Dry powder of hon-shimeji | 1 |
| Flavor | 4.5 |
| Finely divided silicon dioxide | 0.5 |
| Total | 100.0% |

[Formulation Example 7] Gumdrops

| | |
|---|---|
| Sugar | 40 |
| Starch syrup | 30 |
| Glucose syrup | 10 |
| Glycerol | 5 |
| Gelatin | 5 |
| Dry powder of lion's mane mushroom | 5 |
| Flavor | 0.2 |
| Water | balance |
| Total | 100.0% |

[Formulation Example 8] Gumdrops

| | |
|---|---|
| Sugar | 40 |
| Starch syrup | 30 |
| Glucose syrup | 10 |
| Glycerol | 5 |
| Gelatin | 5 |
| Dry maitake powder | 2 |
| Flavor | 0.2 |
| Water | balance |
| Total | 100.0% |

[Formulation Example 9] Dentifrice

| | |
|---|---|
| Silicic anhydride | 15.0 |
| Sodium lauryl sulfate | 1.0 |
| Xanthan gum | 0.5 |
| Sodium alginate | 0.5 |
| Sodium saccharin | 0.1 |
| Sorbitol | 10.0 |

[Formulation Example 9] Dentifrice

| | |
|---|---|
| Xylitol | 5.0 |
| Water extract of lion's mane mushroom | 1.0 |
| (prepared from 10% suspension; | |
| corresponds to dry powder basis concentration of 0.1%) | |
| Flavor | 1.0 |
| Water | balance |
| Total | 100.0% |

[Formulation Example 10] Dentifrice

| | |
|---|---|
| Silicic anhydride | 15.0 |
| Sodium lauryl sulfate | 1.0 |
| Sodium carboxymethylcellulose | 1.0 |
| Carrageenan | 0.5 |
| Sodium saccharin | 0.1 |
| Glycerol | 15.0 |
| Water extract of hon-shimeji | 1.0 |
| (prepared from 10% suspension; | |
| corresponds to dry powder basis concentration of 0.1%) | |
| Flavor | 1.0 |
| Water | balance |
| Total | 100.0% |

[Formulation Example 11] Mouthwash

| | |
|---|---|
| Ethanol | 10.0 |
| Protamine | 0.01 |
| Sorbitol | 5.0 |
| Xylitol | 5.0 |
| Water extract of lion's mane mushroom | 2.0 |
| (prepared from 10% suspension; | |
| corresponds to dry powder basis concentration of 0.2%) | |
| Sodium saccharin | 0.2 |
| Flavor | 0.8 |
| Water | balance |
| Total | 100.0% |

[Formulation Example 12] Mouthwash

| | |
|---|---|
| Xylitol | 5.0 |
| Dry powder of lion's mane mushroom | 0.1 |
| Xanthan gum | 0.15 |
| Flavor | 0.8 |
| Water | balance |
| Total | 100.0% |

[Formulation Example 13] Powder Beverage (for use by dispersing/dissolving in 100 mL of hot or cold water)

| | |
|---|---|
| Powdered green tea | 0.8 |
| Dry powder of lion's mane mushroom | 0.4 |
| Sodium ascorbate | 0.05 |
| Dextrin | 0.05 |
| Total | 1.3 g |

[Formulation Example 14] Powder Beverage (for use by dispersing/dissolving in 100 mL of hot or cold water)

| | |
|---|---|
| Powdered barley tea | 0.8 |
| (Sarasara Kenko Mineral Mugicha ®, from Ito En, Ltd.) | |
| Dry powder of lion's mane mushroom | 0.4 |
| Total | 1.2 g |

[Formulation Example 15] Powder Beverage (for use by dispersing/dissolving in 100 mL of hot or cold water)

| | |
|---|---|
| Powdered roasted green tea | 0.8 |
| (Ooi Ocha Sarasara Hojicha ®, from Ito En, Ltd.) | |
| Dry powder of lion's mane mushroom | 0.4 |
| Total | 1.2 g |

[Formulation Example 16] Powder Beverage (for use by dispersing/dissolving in 100 mL of hot or cold water)

| | |
|---|---|
| Combination bonito/konbu dry soup stock | 0.6 |
| (Hondashi ®, from Ajinomoto Co., Inc.) | |
| Dry powder of lion's mane mushroom | 1.0 |
| Potassium chloride | 0.3 |
| Total | 1.9 g |

The invention claimed is:

1. A method for promoting the growth of non-pathogenic indigenous oral bacteria in a subject in the oral cavity, said method comprising:
administering to the subject an effective amount, for promoting the growth of the non-pathogenic indigenous oral bacteria in the oral cavity, of a dry powder having a concentration of from 0.1 to 20 weight-%, of at least one mushroom selected from the group consisting of lion's mane mushroom (*Hericium erinaceus*), maitake (*Grifola frondosa*), hon-shimeji (*Lyophyllum shimeji*), buna-shimeji (*Hypsizygus marmoreus*), oyster mushroom (*Pleurotus ostreatus*), and agaricus (*Agaricus blazei*),
wherein said dry powder is prepared by freeze-drying or heat drying a mushroom fruiting body or mycelium of said at least one mushroom and then grinding the dried mushroom fruiting body or mycelium of the at least one mushroom, and
wherein the non-pathogenic indigenous oral bacteria are *Mitis* group streptococci selected from the group consisting of *Streptococcus gordonii*, *Streptococcus mitis*, and *Streptococcus oxalis*.

2. The method of claim 1, wherein the dry powder is at least 95 wt % of particles having a size of 500 μm or less.

* * * * *